US008043835B1

(12) United States Patent
Kopreski

(10) Patent No.: US 8,043,835 B1
(45) Date of Patent: *Oct. 25, 2011

(54) METHODS FOR DETECTING AND MONITORING CANCER USING EXTRACELLULAR RNA

(75) Inventor: Michael S. Kopreski, Long Valley, NJ (US)

(73) Assignee: OncoMEDx, Inc., Long Valley, NJ (US)

( * ) Notice: Subject to any disclaimer, the term of this patent is extended or adjusted under 35 U.S.C. 154(b) by 152 days.

This patent is subject to a terminal disclaimer.

(21) Appl. No.: 11/421,260

(22) Filed: May 31, 2006

Related U.S. Application Data

(63) Continuation-in-part of application No. 10/013,868, filed on Oct. 30, 2001, now Pat. No. 6,939,671, which is a continuation of application No. 09/155,152, filed as application No. PCT/US97/03479 on Mar. 14, 1997, now Pat. No. 6,329,179.

(60) Provisional application No. 60/014,730, filed on Mar. 26, 1996.

(51) Int. Cl.
C12P 19/34 (2006.01)
C12Q 1/68 (2006.01)
C07H 21/02 (2006.01)
C07H 21/04 (2006.01)
C07H 21/00 (2006.01)

(52) U.S. Cl. ......... 435/91.2; 435/6; 435/91.1; 536/23.1; 536/24.3; 536/24.33; 536/25.3

(58) Field of Classification Search ............. 435/6, 91.1, 435/91.2, 183; 436/94; 536/23.1, 24.3, 24.33, 536/25.3, 25.32
See application file for complete search history.

(56) References Cited

U.S. PATENT DOCUMENTS

| | | | |
|---|---|---|---|
| 4,350,156 A | 9/1982 | Malchesky | |
| 4,631,130 A | 12/1986 | Watanabe | |
| 4,683,195 A | 7/1987 | Mullis et al. | |
| 4,699,877 A | 10/1987 | Cline et al. | |
| 4,738,927 A | 4/1988 | Taniguchi | |
| 4,839,055 A | 6/1989 | Ishizaki et al. | |
| 4,874,853 A | 10/1989 | Rossi | |
| 4,874,858 A | 10/1989 | Magistro | |
| 4,999,290 A | 3/1991 | Lee | |
| 5,019,243 A | 5/1991 | McEwen et al. | |
| 5,087,617 A | 2/1992 | Smith | |
| 5,098,890 A | 3/1992 | Gewirtz et al. | |
| 5,124,246 A | 6/1992 | Urdea et al. | |
| 5,155,018 A | 10/1992 | Gillespie et al. | |
| 5,217,889 A | 6/1993 | Roninson et al. | |
| 5,274,087 A | 12/1993 | Barnett et al. | |
| 5,300,635 A | 4/1994 | Macfarlane | |
| 5,350,671 A | 9/1994 | Houghton et al. | |
| 5,409,818 A | 4/1995 | Davey et al. | |
| 5,429,923 A | 7/1995 | Seidman | |
| 5,436,318 A | 7/1995 | Reyes et al. | |
| 5,470,724 A | 11/1995 | Ahern | |
| 5,506,106 A | 4/1996 | Croce | |
| 5,532,220 A | 7/1996 | Lee | |
| 5,576,178 A | 11/1996 | Emanuel | |
| 5,994,062 A | 11/1999 | Mulshine et al. | |
| 6,001,987 A | 12/1999 | Perron | |
| 6,051,374 A | 4/2000 | Simons | |
| 6,057,105 A | 5/2000 | Hoon | |
| 6,329,179 B1 | 12/2001 | Kopreski | |
| 6,344,317 B2 | 2/2002 | Urnovitz | |
| 6,607,898 B1 | 8/2003 | Kopreski | |
| 6,656,704 B1 | 12/2003 | Korneluk et al. | |
| 6,759,217 B2 | 7/2004 | Kopreski | |
| 6,794,135 B1 | 9/2004 | Kopreski | |
| 6,916,634 B2 * | 7/2005 | Kopreski ............... | 435/91.2 |
| 6,939,671 B2 | 9/2005 | Kopreski | |
| 2004/0014079 A1 | 1/2004 | Kopreski et al. | |
| 2004/0058331 A1 | 3/2004 | Akagi | |
| 2006/0286578 A1 * | 12/2006 | Kopreski et al. ........ | 435/6 |
| 2008/0096217 A1 | 4/2008 | Kopreski | |
| 2008/0207723 A1 | 8/2008 | Kopreski | |
| 2010/0144832 A1 | 6/2010 | Srivastava et al. | |

FOREIGN PATENT DOCUMENTS

| | | |
|---|---|---|
| DE | 3717212 | 9/2003 |
| WO | WO 90/09456 A1 | 8/1990 |
| WO | 97/35589 A | 10/1997 |
| WO | WO 97/35589 A | 10/1997 |
| WO | WO 98/14617 A | 10/1997 |
| WO | 98/14617 A | 4/1998 |
| WO | 99/67397 | 12/1999 |

OTHER PUBLICATIONS

Pelosi et al., Detecting cell-free circulating hTERT mRNA in the plasma may identify a subset of nonsmall cell lung cancer patients. Virchows Arch., 448, 7-15, 2006.*

Kopreski et al., Circulating RNA as a Tumor Marker: Detection of 5T4 mRNA in Breast and Lung Cancer Patient Serum. Annals of the New York Academy of Science, 945, 172-178, 2001.*

Tahara et al., Immuno-histochemical detection of human telomerase catalytic component, hTERT, in human colorectal tumor and non-tumor tissue sections. Oncogene, 18, 1561-1567, 1999.*

(Continued)

Primary Examiner — Frank W Lu
(74) Attorney, Agent, or Firm — McDonnell Boehnen Hulbert & Berghoff

(57) ABSTRACT

The invention provides methods, reagents and kits for using extracellular RNA in bodily fluids including plasma and serum to detect, infer, or monitor diseases such as cancer and other neoplasia.

2 Claims, No Drawings

OTHER PUBLICATIONS

Rohde et al., Expression of the Human Telomerase Reverse Transcriptase Is Not Related to Telomerase Activity in Normal and Malignant Renal Tissue. Clinical Cancer Research, 6, 4803-4809, 2000. Southall et al.,Immunohistological distribution of 5T4 antigen in normal and malignant tissues. Br. J. Cancer, 61, 89-95, 1990.*
Lledo et al., Real time quantification in plasma of human telomerase reverse transcriptase (hTERT) mRNA in patients with colorectal cancer. Colorectal Disease, 6, 236-242, 2004.*
Wong et al., Quantification of Plasma β-Catenin mRNA in Colorectal Cancer and Adenoma Patients. Clinical Cancer Research,10,1613-1617, 2004.*
Abravaya et al., "Detection of point mutations with a modified ligase chain reaction (GAP-LCR)," *Nucleic Acids Research* 23:675-682 (1995).
Alkema et al., "Characterization and Chromosamal Localization of the Human Prata-Oncogene BMI-1," *Human Mol Genet* 2:1597-1603 (1993).
Aoki et al., "Liposome-mediated in viva gene transfer on antisense K-ras construct inhibits pancreatic tumor dissemination in the murine peritoneal cavity," *Cancer Research* 55:3810-3816 (1995).
Barz et al., "Characterization of Cellular and Extracellular Plasma Membrane Vesicles from a Non-metastasing Lymphoma (Eb) and Its Metastasing Variant (Esb)," *Biochin Biophys Acta* 814:77-84 (1985).
Bauer et al., "Identification of H-2Kb Binding and Immunogenic Peptides from Human Papillama Virus Tumour Antigens E6 and E7," *Scand J Immunol* 42:317-323 (1995).
Blackburn et al., "Electrochemiluminescence detection for development of immunoassays and DNA probe assays for clinical diagnostics," *Olin Chem* 37/9:1534-1539 (1991).
Bobo et al., "Diagnosis of chlamydia trachomatis cervical infection by detection of amplified DNA with an enzyme immunoassay," *J din Micra* 28:1968-1973 (1990).
Bocchia et al., "Specific Binding of Leukemia Oncogene Fusion Peptides to HLA Class I Molecules," *Blood* 85:2680-2684 (1995).
Boom et al., "Rapid and Simple Method for Purification of Nucleic Acids," *J Clin Micro* 28:495-503 (1990).
Boom et al., "Rapid Purification of Hepatitis B Virus DNA from Seruc," *J Clin Micro* 29:180-181 (1991).
Brossart et al., "Detection of residual tumor cells in patients with malignant melanoma responding to immunotherapy," *J Immunotherapy* 15:38-41 (1994.
Buchman et al., "Selective RNA amplification: A novel method using d UMP-containing primers and uracil DNA glycosylase," *PCR Methods Applic* 3:28-31 (1993).
Carr et al., "Circulating Membrane Vesicles in Leukemic Blood," *Cancer Research* 45:5944-5951 (1985).
Cheung et al., "Rapid and Sensitive Method for Detection of Hepatitis C Virus RNA by Using Silica Particles," *J Clin Micro* 32:2593-2597 (1994).
Chirgwin et al., "Isolation of biologically active ribonucleic acid from sources enriched in ribonuclease," *Biochemistry* 18:5294-5299 (1979).
Chomczynski and Mackey, "Modification of the TRI reagent (TM) procedure for isolation of RNA from polysaccaride- and proteaglycan-rich sources," *BioTechniques* 19:942-945 (1995).
Chomczynski and Mackey, "Substitution of chloroform by bromo-chloropropane in the single-step method of RNA isolation," *Analytical Biochemistry* 225:163-164 (1995).
Chomczynski et al., "Single-step method of RNA isolation by acid guanidinium thiocyanate-phenol-chloroform extraction," *Analytical Biochemistry* 162:156-159 (1987).
Chomczynski, "A reagent for the single-step simultaneous isolation of RNA, DNA and proteins from cell and tissue samples," *Biotech* 15:532-537 (1993).
Chu et al., "Thymidylate synthase binds to c-myc RNA in human colon cancer cells and in vitro," *Mol Cell Biol* 15:179-185 (1995).
Cohen, "Biochemical Therapy: Antisense Compounds," *In: Biologic Teraphy of Cancer* (DeVita, Hellman, Rosenberg, eds) J.B. Lippincott, Ca., Philadelphia (1991) pp. 763-775.

Colomer et al., "erB-2 antisense oligonucleotides inhibit the proliferation of breast carcinoma cells with erb-2 oncogene amplification," *Br J Cancer* 70:819-825 (1994).
Coutlee et al., "Immunodetection of DNA with biotinylated RNA probes: A study of reactivity of a monoclonal antibody to DNA-RNA hybrids," *Analytical Biochemistry* 181:96-105 (1989).
Datta et al., "Sensitive Detection of Occult Breast Cancer by the Reverse-transcriptase Polymerase Chain Reaction," *Journal of Clinical Oncology* 12:475-482 (1994).
Davidova and Shapot, "Liporibonucleoprotein Complex as an Integral Part of Animal Cell Plasma Membranes," *FEBS Lett* 6:349-351 (1970).
DiCesare et al., "A high-sensitivity electrochemiluminescense-based detection system for automated PCR product quantitation," *BioTechniques* 15:152-157 (1993).
Doi et al., "Detection of beta-human chorionic ganadotropin mRNA as a marker for cutaneoud malignant melanoma," *Int J Cancer* 65:454-45-. (1996).
Dosaka et al., "A complex pattern of translational initiation and phosphorylation in L-Myc Proteins," *Oncogene* 6:371-378 (1991).
Edmands et al., "Rapid RT-PCR Amplification from Limited Cell Numbers," *PCR Methods Applic* 3:317-319 (1994).
Feng et al., "The RNA component of human telomerase," *Science* 269:1236-1241 (1995).
Fournie et al., "Recovery of nanogram quantities of DNA from plasma and quantitative measurement using labeling by nick translation," *Analytical Biochemistry* 158:250-256 (1986).
Gerhard et al., "Specific detection of carcinoembryonic antigen-expressing tumor cells in bone marrow aspirates by polymerase chain reaction," *J Clin Oncol* 12:725-729 (1994).
Ghossein et al., "Detection of Circulating Tumor Cells in Patients with Localized and Metastatic Prostatic Carcinoma: Clinical Implications," *Journal of Clinical Oncology* 13:1195-1200 (1995).
Higashiyama et al., "Reduced Motility Related Protein-1 (MRP-1/CD9) Gene Expression as a Factor of Poor Prognosis in Non-small Cell Lung Cancer," *Cancer Research* 55:6040-6044 (1995).
Hoon et al., "Detection of occult melanoma cells in blood with a multiple-marker polymerase chain reaction assay," *J Clin Oncol* 13:2109-2116 (1995).
Hoover et al., "Immunatherapy by Active Specific Immunization: Clinical Applications," *In: Biologic-Therapy of Cancer* (DeVita, Hellman, Rosenberg, eds) J.B. Lippincott, Co., Philadelphia (1991) pp. 670-682.
Imai et al., "Detection of HIV-1 RNA in Heparinized Plasma of HIV-1 Seropositive Individuals," *J Virol Methods* 36:181-184 (1992).
Jrdea et al., "Direct and quantitative detection of HIV-I RNA in human plasma with a branched DNA signal amplification assay," *AIDS* 7(suppl 2):S11-514 (1993).
Juckett and Rosenberg, "Actions of Cis-diamminedichloroplatinum on Cell Surface Nucleic Acids in Cancer Cells as Determined by Cell Electrophoresis Techniques," *Cancer Research* 42:3565-3573 (1982).
Kahn et al., "Rapid and sensitive nonradioactive detection of mutant K-ras genes via enriched PCR amplification," *Oncogene* 6:1079-1083 (1991).
Kamm and Smith, "Nucleic acid concentrations in normal human plasma," *Clinical Chemistry* 8:519-522 (1972).
Karet et al., "Quantification of mRNA in human tissue using fluorescent nested reverse-transcriptase polymerase chain reaction," *Analytical Biochemistry* 220:384-390 (1994).
Katz et al., "Enhanced Reverse Transcriptase-Polymerase Chain Reaction for Prostate Specific Antigen as a Indicator of True Pathologic Stage in Patients with Prostate Cancer," *Cancer* 75:1642-1648 (1995).
Kievits et al., "NASBA(TM) isothermal enzymatic in vitro nucleic acid amplification optimized for the diagnosis of HIV-1 infection," *J Virological Methods* 35:273-286 (1991).
Kim et al., "Specific association of human telomerase activity with immortal cells and cancer," *Science* 266:2011-2015 (1994).
Komeda et al., "Sensitive detection of circulating heptocellular carcinoma cells in peripheral venous load," *Cancer* 75:2214-2219 (1995).

Landgraf et al., "Direct analysis of polymerase chain reaction products using enzyme-linked immunasorbent assay techniques," *Analytical Biochmistry* 198:86-91 (1991).

Landgraf et al., "Quantitative analysis of polymerase chain reaction (PCR) products using primers labeled with biotin and a fluorescent dye," *Analytical Biochemistry* 193:231-235 (1991).

Larson et al., "Radioisotope Conjugates," *In: Biologic Therapy of Cancer* (DeVita, Hellman, Rosenberg, eds) J.B. Lippincott, Co., Philadelphia (1991) pp. 496-511.

Leon et al., "A Comparison of DNA and DNA-binding Protein Levels in Malignant Disease," *Europ J Cancer* 17:533-538 (1981).

Maruyama et al., "Detection of AMLi/ETO fusion transcript as a tool for diagnosing t(8;21) positive acute myelogenous leukemia," *Leukemia* 8:40-45 (1994).

Masella et al., "Characterization of Vesicles, Containing an Acylated Oligopeptide, Released by Human Colon Adenocarcinoma Cells," *FEBS Lett* 246:25-29 (1989).

McCabe et al., "Minimal Determinant Expressed by a Recombinant Viaccinia Virus Elicits Therapeutic Antitumor Cytolytic T Lumphocyte Responses," *Cancer Research* 55:1741-1747 (1995).

Miller et al., "Detection of minimal residual disease in acute promyelocytic leukemia by a reverse transcription polymerase chain reaction assay for the PML/RAR-alpha fusion mRNA," *Blood* 82:1689-1694 (1993).

Moore et al., "Design of PCR primers that detect only mRNA in the presence of DNA," *Nucleic Acids Research* 18:1921 (1991).

Mori, et al., "Detection of Cancer Micrometastases in Lymph Nodes by Reverse Transcriptase-Polymerase Chain Reaction," *Cancer Research* 55:3417-3420 (1995).

Mountford et al., "Proteolipid Identified by Magnetic Resonance Spectroscopy in Plasma of a Patient with Borderline Ovarian Tumor," *Lancet* i:829-834 (1987).

Nguyen, "Southern blot analysis of polymerase chain reaction products on acrylamide gels," *BioTechniques* 7:238-240 (1989).

Ozcelik et al., "Low Levels of Expression of an Inhibitor of Cyclin-dependent Kinases (CIP1/WAF1) in Primary Breast Carcinomas with p53 Mutations," *Clinical Cancer Research* 1:907-912 (1995).

Patard et al., "Expression of MAGE genes in transitional-cell carcinomas of the urinary bladder," *mt J Cancer* 64:60-64 (1995).

Penno et al., "Expression of CD44 in human lung tumors," *Cancer Research* 54:1381-1387 (1994).

Peoples et al., "Breast and Ovarian Cancer-Specific Cytotoxic T Lymphocytes Recognize the same HER-2/Neu Derived Peptide," *Proc Natl Acad Sci USA* 92:432-436 (1995).

Pfleiderer et al., "Detection of tumor cells in peripheral blood and bone marrow from ewing tumor patients by RT-PCR," *Int J Cancer (Pred. Oncol)* 64:135-139 (1995).

Polushin et al., "Antisense Pro-Drugs: 5'-ester oligodeoxynucleotides," *Nucleic Acids Research* 22:5492-5496 (1994).

Rashtchian, "Amplification of RNA," *PCR Methods Applic* 4:S83-S91 (1994).

Reddi and Holland, "Elevated Serum Ribonuclease in Patients with Pancreatic Cancer," *Proc Nat Acad Sci USA* 73:2308-2310 (1976).

Rieber and Bacalao, "An 'external' RNS removable from mammalian cells by mild proteolysis," *Proc Natl Acad Sci USA* 71:4960-4964 (1974).

Roggenbuck et al., "Human Papillomavirus Type 18 E6 and E6, and E7 Protein Synthesis in Cell Free Translation Systems and Comparison of E6 and E7 in Vitro Translation Products to Proteins Immunoprecipitated from Human Epthelial Cells," *J Viral* 65:5068-72 (1991).

Rosenberg-Nicolson et al., "Nucleoprotein Complexes Released from Lymphoma Nuclei that Contain the abl Oncogene and RNA and DNA Polymerase and RNA Primase Activities," *J Cell Biochem* 50:43-52 (1992).

Rosi et al., "RNA-Lipid Complexes Released from the Plasma Membrane of Human Colon Carcinoma Cells," *Cancer Lett* 39:153-160 (1988).

Saiki et al., "Genetic analysis of amplified DNA with immobilized sequence-specific oligonucleotide probes," *Science* 233:1076-1078 (1989).

Sakakura et al., "Inhibition of gastric cancer cell proliferation by antisense oligonucleotides targeting the messenger RNA encoding proliferating cell nuclear antigen," *Br J Cancer* 70:1060-1066 (1994).

Schlom, "Antibodies in cancer therapy: basic principles of monaclanal antibodies," *In: Biologic Therapy of Cancer*, (DeVita, Hellman, Hellman, Rosenberg, eds) J.B. Lippincott, Co., Philadelphia (1991) pp. 464-481.

Shea et al., "Identification of the Human Prostate Carcinoma Onogene PTI-1 by Rapid Expression Cloning and Differential RNA Display," *Proc Natl Acad Sci USA* 92:6778-6782 (1995).

Skorski et al., "Suppression of philadelphial leukemia cell growth in mice by BORABL antisense oligodeoxynucleotide," *Proc Natl Acad Sci USA* 91:4504-4508 (1994).

Smith et al., "Detection of Melanoma Cells in Peripheral Blood by Means of Reverse Transcriptase and Polymerase Chain Reaction," *Lancet* 338:1227-1229 (1991).

Sooknanan et al., "Detection and direct sequence identification of BCR-ABL mRNA in Ph+ chronic myeloid leukemia," *Experimental Hematology* 21:1718-1724 (1993).

Stock et al., "Value of molecular monitoring during the treatment of chronic myeloid leukemia: A cancer and leukemia group B study," *J Olin Oncology* 15:26-36 (1997).

Stroun et al., "Neoplastic characteristics of the DNA found in the plasma of cancer patients," *Oncology* 46:318-322 (1989).

Taylor and Blak, "Shedding of Plasma Membrane Fragments. Neoplastic and Developmental Importance," *In: The Cell Surface in Development and Cancer, Develop Biol* 3:33-57 Editor: M.S. Steinberg. Plenum Press, New York, London (1985).

Urdea et al., "Branched DNA amplification multimers for the sensitive, direct detection of human hepatitis viruses," *Nucleic Acids Research Symposium Series* 24:197-200 (1991).

Vandamme et al., "Detection of HIV-1 RNA in plasma and serum samples using the NASBA amplification system compared to RNA-PCR," *J Virological Methods* 52:121-132 (1995).

Vitetta et al., "Immunatoxins," *In: Biologic Therapy of Cancer* (DeVita, Hellman, Rosenberg, eds) J.B. Lippincott, Co., Philadelphia (1991) pp. 482-495.

Wang et al., "Quantitation of mRNA by the polymerase chain reaction," *Proc Natl Aced Sci USA* 86:9717-9721 (1989).

Wieczorek et al., "Diagnostic and Prognostic Value of RNA-Proteolipid in Sera of Patients with Malignant Disorders Following Therapy; First Clinical Evaluation of a Novel Tumor Marker," *Cancer Research* 47:6407-6412 (1987).

Wieczorek et al., "Gensondentest Fur RNA-Proteolipid in Serumproben Bei Neoplasie," *Schweiz med Wschr* 119:1342-1343 (1989).

Wieczorek et al., "Isolation and Characterization of an RNA-Proteolipid Complex Associated with the Malignant State in Humans," *Proc Natl Aced Sci USA* 82:3455-3459 (1985).

Wiedmann et al., "Ligase chain reaction (LCR)—overview and applications," *POR Methods Applic* 3:551-564 (1994).

Yanuck et al., "A Mutant P53 Tumor Suppressor Protein is a Target f or Peptide-Induced 0DB' Cytotoxic T-Cells," *Cancer Research* 52:3257-3261 (1993).

Kopreski et al., "Detection of tumor messenger RNA in the serum of patients with malignant melanoma." Clinical Cancer Research 5:1961-65 (Aug. 1999) 5:1961-65.

Leitzel et a., "Detection of cancer cells in peripheral blood of breast cancer patients using reverse transcription-polymerase chain reaction for epidermal growth factor receptor." Clinical Cancer Research 4:3037-43 (Dec. 1998).

Tamamiyagi et al., "Quantitative analysis of ferrochelatase mRNA in blood cells of erythropoietic protoprophyria patients." Journal of Dermatological Science 11(2)154-60 (Feb. 1996).

Garbarz et al.,"Spectrin Beta-Tandil A Novel Shortened Beta-Chain Variant Associated with Hereditary Elliptocytosis is due to a Deletional Frameshift Mutation in the Beta Spectrin Gene," Blood 80(4)1066-73 (1992).

Monteyne et al., "Expression of costimulatory molecules and cytokines in CSF and peripheral blood mononuclear cells from multiple sclerosis patients" Acta Neurological Belgica 1(99):11-20 (Mar. 1999).

Serra et al., "Multiple sclerosis and multiple sclerosis-associated retrovirus in Sardinia" Neurological Sciences 22(2)171-73 (Apr. 2001).
Kopreski et al., "Cellular-versus extracellular-based assays. Comparing utility in DNA and RNA molecular marker assessment" Annals of New York Academy of Sciences 906:124-8 (Apr. 2000).
Messner et al., "Expression of messenger RNA of the cardiac isoforms of troponin T and I in myopathic skeletal muscle" American Journal of Clinical Pathology 114(4)544-49(Oct. 2000).
Kamm et al., "Nucleic-Acid Concentrations in Normal Human Plasma" Clinical Chemistry 18(6)519-22 (1972).
Shutack et al., "A Study of the RNA levels of normal blood serum" The Journal of the American Osteopathic Association 67(9)1051-53 (May 1968).
Lasheeb et al., "Semen characteristics in HIV-1 positive men and the effect of semen washing" Genitourinary Medicine 73(4) 303-305 (1997).
Mermin et al., "Detection of human immunodeficiency virus DNA and RNA in semen by the polymerase chain reaction." Journ. of Infectious Diseases 164(4)769-772 (Oct. 1991).
Monteyne et al., "Expression of costimulatory molecules and cytokines in CSF and peripheral blood mononuclear cells from multiple sclerosis patients." ACTA. Neurologica Belgica 99(1)11-20 (Mar. 1999).
Guin et al., "Electrophoretic Characterization of Plasma RNA" Biochemical Medicine 13(3)224-230 (1975).
Stroun et al., "Presence of RNA in the nucleoprotein complex spontaneously released by human lymphocytes and frog auricles in culture," Cancer Research 38(10)3546-54 (Oct. 1978).
Alloche et al. "Expression of basic fibroblast growth factor (bFGF) and FGF-receptors in human leukemic cells" Leukemia: Official Journal of the Leukemia Society of America, Leukemia Research Fund, 9(1)77-86 (Jan. 1995).
Rosenzweig et al., "Preclinical Diagnosis of Familial Hypertrophic Cardiomyopathy by Genetic Analysis of Blood Lymphocytes" New England Journal of Medicine 325(25)1753-60 (Nov. 19, 1981).
Spiegelman et al., "The Development and Use of and Extracellular RNA Replicating System" The Harvey Lectures No. 64 Delivered under the Auspices of the Harvey Society of New York 1969.
Serra et al. (2001), Neurological Sciences 22(2): 171-173.
Shen et al. (1995), Proc. Natl. Acad. Sci. U. S. A. 92: 6778-6782.
Shutack et al. (1968), J. Am. Osteopath. Assoc. 67(9): 1051-1053.
Stroun et al. (1978), Cancer Res. 38(10): 3546-3554.
Tamamiyagi et al. (1996), J. Dermatol. Sci. 11(2): 154-60.
Urdea et al. (1993), AIDS 7(suppl. 2): S11-S14.
Rohde et al. (2000), Clin. Cancer Res. 6: 4803-4809.
Keller et al. (1993), PCR Methods and Applications 3: 32-38.
Nolte et al. (1994), J. Clin. Microbiology 32: 519-520.
Schmidt et al. (1995), J. Med. Virology 47: 153-160.
Agliullina et al. (1988), Eksp. Onkol (USSR) 10(4), English abstract.
Schwarz et al. (1995), Res. Virol (Paris) 146(5), English abstract.
Kato et al. (1993), Hepatology 18(1), abstract.
Glick et al. (1994), Molecular biotechnology: Principles and applications of recombinant DNA, ASM Press: Washington DC. Table of Contents for Molecular Diagnostics (8) and Vaccines and Therapeutic Agents (9).
Persing et al (1993), Diagnostic molecular microbiology: Principles and applications, Amer. Soc. Microbiol. Washington DC, Table of Contents for Principles of Diagnostic Molecular Microbiology and Viral Pathogens.
Southall et al. (1990), Br. J. Cancer 61: 89-95.
Kopreski et al. (2001), Ann. N. Y. Acad. Sci 945: 172-178.
Yan-Sanders et al. (2002), Cancer Letters 183: 215-220.
Khimani et al. (2005), BioTechniques 38: 739-745.
Schrader et al. (2002), BMC Cancer 2: 32.
Fleischhacker et al. (2001), Ann. N. Y. Acad. Sci. 945: 179-188.
Burd et al. (1989), Proc. Natl. Acad. Sci. U. S. A. 86: 9788-9792.
Burchill et al. (1995), Br. J. Cancer 71: 278-281.
Lasheeb et al. (1997), Genitourinary Medicine 73(4): 303-305.
Mermin et al. (1991), J. Infectious Diseases 164(4): 769-772.
Kopreski et al. (2001), Clin. Chem. 47: 362, abstract 9.
Pelosi et al. (2006), Virchows Arch. 448: 7-15.
Tahara et al. (1999), Oncogene 18: 1561-1567.
Dasi et al. (2001), Lab. Investigation 81: 767-769.
Hasselmann et al. (2001), Oncol. Rep. 8: 115-118.
Ng et al. (2002), Clin. Chem. 48: 1212-1217.
Chen et al. (2000), Clin. Cancer Res. 6: 3823-3826.
Silva et al. (2001), Clin. Cancer Res. 7: 2821-2825.
Silva et al. (2001), Oncol. Rep. 8: 693-696.
Gal et al. (2001), Ann. N. Y. Acad. Sci. 945: 192-194.
Miura et al. (2003), Oncology 64: 430-434.
Wong et al. (2004), J. Clin. Pathol. 57: 766-768.
Ma et al. (2007), Haematologica 92: 170-175.
Arcari et al. (1984), Nucleic Acids Res. 12: 9179-9189.
Rykova et al. (2006), Ann. N. Y. Acad. Sci. 1075: 328-333.
Hernandez et al. (1999), Leukemia 13: 2087-2093.
Zhou et al. (1998), Clin. Cancer Res. 4: 1631-1640.
Zhou et al. (2001), Breast Cancer Research and Treatment 66: 217-224.
Press et al. (1990), Oncogene 5: 953-962.
Ng et al. (2003), Proc. Natl. Acad. Sci. U. S. A. 100: 4748-4753.
Ba Ray et al. (2002), Arch. Pathol. Lab. Med. 126: 574-576.
Gilmour et al. (2001), Cancer Res. 61: 2169-2716.
Reinhold et al. (2001), Clin. Chem. 47: 369, abstract 50.
Messner et al. (2000), Am. J. Clin. Pathol. 114(4): 544-549.
Monteyne et al. (1999), Acta Neurol. Belg. 99(1): 11-20.
Moreno et al. (1992), Cancer Res. 52: 5110-5112.
Rajagopal et al. (1995), Int. J. Cancer 62: 661-667.
Dahiya et al. (1996), Urology 48: 963-970.
LeRiche et al. (1996), J. Clin. Endocrinol. Metab. 81: 656-662.
Pfeiffer et al. (1997), Int. J. Cancer 72: 581-586.
De Luca et al. (2000), Clin. Cancer Res. 6: 1439-1444.
Schlegel et al. (1994), Int. J. Cancer 56: 72-77.
Worm et al. (1999), Hum. Pathol. 30: 222-227.
Pawlowski et al. (2000), Cancer Detect. Prev. 24: 212-223.
Walch et al. (2001), Lab. Invest. 81: 791-801.
Sarkar et al. (1993), Diagn. Mol. Pathol. 2: 210-218.
Gebhardt et al. (1998), Biochem. Biophys. Res. Comm. 247: 319-323.
Revillion et al. (1997), Clin. Chem. 43: 2114-2120.
Schneeberger et al. (1996), Anticancer Res. 16: 849-852.
Kraehn et al. (2001), Br. J. Cancer 84: 72-79.
Gamberi et al. (1998), Oncology 55: 556-563.
Sagawa et al. (2001), Cancer Letters 168: 45-50.
Christoph et al. (1999). Int. J. Cancer 84: 169-173.
Latil et al. (2000), Int. J. Cancer 89: 172-176.
Zhou et al. (1996), J. Biol. Chem. 271: 10760-10766.
Kozu et al. (1995), Genomics 25: 365-371.
Gocke et al. (2001), Clin. Chem. 47: 369, abstract 51.
Poon et al. (2001), Clin. Chem. 47: 363, abstract 11.
Urnovitz et al. (1999), Clin. Diag. Lab. Immunology 6: 330-335.
Zhao et al. (1994), Circulation 90: 677-685.
Dhillon et al. (2001), Exp. Neurol. 170: 140-148.
Fleischhacker et al. (2001), Clin. Chem. 47: 369 (Oral Presentation).
El-Hefnawy et al. (2004), Clin. Chem. 50(3): 564-573.
Tschentscher et al. (2000), Int. J. Clin. Lab. Res. 30(1): 13-15.
Missov et al. (1999), Clinica Chimica Acta 284: 175-185.
Sarko et al. (2002), J. Emerg. Med. 23(1): 57-65.
Jurlander et al. (2000), Eur. Heart J. 21: 382-289.
Rainer et al. (2003), Clin. Chem. 50(1): 206-208.
Townsend et al. (1995), J. Mol. Cell. Cardiol. 27: 2223-2236.
Mizuno et al. (2001), Blood 97(5): 1172-1179.
Meikl et al. (1998), Leukemia 12: 311-316.
Eads et al. (1999), Cancer Res. 59: 2302-2306.
Robertson et al. (1999), Nucleic Acids Res. 27(11): 2291-2298.
Fleischhacker and Schmidt (2007), Biochim. Biophys. Acta 1775: 181-232.
Lion et al. (1995), Leukemia 9: 1353-1360.
El-Deiry, et al. (1991), Proc. Natl. Acad. Sci. U. S. A. 88: 3470-3474.
Lo et al. (1999), Clin. Chem. 45(8): 1292-1294.
Chen et al. (1999), Int. J. Cancer 83: 10-14.
Saito et al. (2001), Hepatology 33: 561-568.
Allouche et al. (1995), Leukemia 9(1): 77-86.
Garbarz et al. (1992), Blood 80(4): 1066-1073.
Guin et al. (1975), Biochemical Medicine 13(3): 224-230.
Kopreski et al. (1999), Clin. Cancer Res. 5: 1961-1965.

Kopreski et al. (2000), Ann. N. Y. Acad. Sci. 906: 124-128.

Leitzel et al. (1998), Clin. Cancer Res. 4: 3037-3043.

Baier et al. (1993), "Improved specificity of RT-PCR amplification using nested cDNA primers." Nucleic Acids Research 21: 1329-30.

Bairey et al. (2002), "Lack of HER-2/neu expression in Hodgkin and non-Hodgkin lymphoma," Arch. Pathol. Lab. Med. 126: 574-576.

Begum et al. (1996), "Loss of hIRH mRNA expression from premalignant adenomas and malignant cell lines." Biochemical and Biophysical Research Communications 229: 864-8.

Carpenter et al. (2006), "The roles of heterogeneous nuclear ribonucleoproteins in tumour development and progression." Biochimica et Biophysica Acta 1765: 85-100.

Definition of "BRC-ABL fusion gene" from ncbi.nlm.nih.gov, printed on Jun. 18, 2010.

Definition of "erbB" from Wikipedia, accessed on Sep. 13, 2009.

Definition of "extracellular" from Wikipedia, accessed on May 15, 2009.

Definition of "intracellular" from Wikipedia, accessed on May 15, 2009.

Definition of "Myc" from Wikipedia, accessed on Sep. 15, 2008.

Definitions of "oncogene" from Google search, accessed on Aug. 3, 2007.

Definition of "precancerous (premalignant) condition" from Wikipedia, accessed on Apr. 20, 2009.

Durie et al. (2000), "RT-PCR amplicons in the plasma of multiple myeloma patients—clinical relevance and molecular pathology," Acta Oncol. 39: 789-796.

Kolquist et al. (1998), "Expression of TERT in early premalignant lesions and a subset of cells in normal tissues." Nature Genetics 19: 182-6.

Lapointe et al. (2007), "A variant TMPRSS2 isoform and ERG fusion product in prostate cancer with implications for molecular diagnosis." Modern Pathology 20: 467-73.

Laxman et al. (2006), "Noninvasive detection of TMPRSS2:ERG fusion transcripts in the urine of men with prostate cancer." Neoplasia 8(10): 885-8.

Lee et al. (1996), "Limited up-regulation of DNA methyltransferase in human colon cancer reflecting increased cell proliferation," Proc. Natl. Acad. Sci. U. S. A. 93: 10366-10370.

Melki et al. (1998), "Increased DNA methyltransferase expression in leukaemia," Leukemia 12(3): 311-316.

Müller et al. (2001), "Ubiquitous expression of the calcitonin-i gene in multiple tissues in response to sepsis." J. Clin. Endocrinol. Metab. 86(1): 396-404.

Ng et al. (2004), "Evaluation of human chorionic gonadotropin beta-subunit mRNA concentrations in maternal serum in aneuploid pregnancies: a feasibility study." Clinical Chemistry 50: 1055-7.

"Principle of cycling probe technology," description from Takara Bio Inc. website, printed May 1, 2009.

Ricchiuti et al. (1997), "Cardiac troponin I and T alterations in hearts with severe left ventricular remodeling." Clin. Chem. 43(6): 990-995.

Ricchiuti et al. (1999), "Expression of cardiac troponin T mRNA in skeletal muscle from patients with end stage renal disease and muscular dystrophy." Clin. Chem. 45(6), Suppl.:A144-A145.

Ricchiuti et al. (1999), "RNA expression of cardiac troponin T isoforms in diseased human skeletal muscle." Clin. Chem. 45(12): 2129-2135.

Schüler et al. (2003), "Chromosomal translocation t(14;18) in healthy individuals." Semin. Cancer Biol. 13(3): 203-9.

Shibuta et al. (2002), "Regional expression of CXCL 12/CXCR4 in liver and hepatocellular carcinoma and cell-cycle variation during in vitro differentiation." Jpn. J. Cancer Res. 93: 789-97.

Steketee et al. (1997), "Early detection of perinatal human immunodeficiency virus (HIV) type 1 infection using HIV RNA amplification and detection. New York City Perinatal HIV Transmission Collaborative Study." J. Infect. Dis. 175(3): 707-11.

Stroun et al. (1989), "Neoplastic characteristics of the DNA found in the plasma of cancer patients," Oncology 46: 318-322.

Sueoka et al. (2005), "Detection of plasma hnRNP B1 mRNA, a new cancer biomarker, in lung cancer patients by quantitative real-time polymerase chain reaction." Lung Cancer 48: 77-83.

Takamiyagi et al. (1996), "Quantitative analysis of ferrochelatase mRNA in blood cells of erythropoietic protoporphyria patients." J. Dermatol. Sci. 11(2): 154-60.

Tsui et al. (2002), "Stability of endogenous and added RNA in blood specimens, serum, and plasma," Clin. Chem. 48: 1647-1653.

Tsukahara et al. (1998), "Expression of inducible nitric oxide synthase in circulating neutrophils of the systemic inflammatory response syndrome and septic patients." World Journal of Surgery 22(8): 771-7.

Wagner et al. (1995), "Patterns of p53, erbB-2, and EGF-r expression in premalignant lesions of the urinary bladder." Human Pathology 26: 970-8.

Wong et al. (2006), "Plasma RNA integrity analysis: methodology and validation," Ann. N. Y. Acad. Sci. 1075: 174-178.

Zhou et al. (2008), "Circulating RNA as a novel tumor marker: an in vitro study of the origins and characteristics of extracellular RNA," Cancer Letters 259: 50-60.

Kanbara et al., "Clinical significance of serum AFP-mRNA in the hepatocellular carcinoma (HCC) patient" International Hepatology Communications (Jul. 1995) 3, p. S155-S155.

\* cited by examiner

METHODS FOR DETECTING AND MONITORING CANCER USING EXTRACELLULAR RNA

This application is a continuation-in-part of U.S. Ser. No. 10/013,868, filed Oct. 30, 2001, now U.S. Pat. No. 6,939,671, which is a continuation of U.S. patent application Ser. No. 09/155,152, filed Sep. 22, 1998, now U.S. Pat. No. 6,329,179 B1, which is U.S. national phase application filed pursuant to the provisions of 35 U.S.C. §371 of International Application, Serial No. PCT/US97/03479, filed Mar. 14, 1997, which claims the benefit of the filing date of Provisional U.S. patent application Ser. No. 60/014,730, filed Mar. 26, 1996, the entire disclosure of each of which is hereby incorporated by reference.

BACKGROUND OF THE INVENTION

Ribonucleic acid (RNA) plays an essential role in the translation of the genetic code to produce proteins necessary for cellular function, both in normal cells and neoplastic or diseased cells. In particular, RNA including transfer RNA, messenger RNA or messenger-like RNA, and ribosomal RNA carry and translate the genetic code to sites of protein production. Further, double-stranded RNA plays an important role in silencing genetic expression. Other RNA species are found within ribonucleoproteins. For example, telomerase RNA is a critical component of telomerase, an important ribonucleoprotein highly expressed in most cancers. The pathogenesis and regulation of cancer is thus dependent upon RNA-mediated translation of specific genetic code, often reflecting mutational events or other alterations within deoxyribonucleic acid (DNA), including epigentic alterations such as hypermethylation, microsatellite alterations, loss of heterozygosity, translocations, deletions, and point mutations. Further, other RNA species and their associated proteins, although not necessarily being directly involved in neoplastic pathogenesis or regulation, may provide recognizable characterization of neoplasia or disease by being inappropriately expressed or elevated. Such overexpression of RNA thus can delineate cancer or other disease. Recognition of the presence or overexpression of specific RNA can enable identification, detection, inference, monitoring, or evaluation of any neoplasm, whether benign, malignant, or premalignant, in humans and animals.

U.S. Pat. No. 6,329,179 B1, incorporated herein in its entirety, teaches that both tumor-associated and non-tumor associated RNA are detectable in plasma and serum. Total RNA, to be understood in cancer patient to comprise both tumor-associated and non-tumor-associated RNA and further being heterogeneous RNA, can be extracted from plasma or serum, the RNA of interest or its cDNA is amplified qualitatively or quantitatively, and the amplified product of an RNA or cDNA species of interest detected. Of particular note, U.S. Pat. No. 6,329,179 B1 teaches that extracellular RNA is present in greater amount when obtained from cancer patients than from healthy individuals, Subsequent art supports these teachings by demonstrating that extracellular RNA of various RNA species are detectable in bodily fluids, for example in co-owned U.S. Pat. No. 6,607,898; Kopreski et al., 1999, *Clin. Cancer Res.* 5: 1961-1965; Dasi et al., 2001, *Lab, investigation* 81: 767-769; Hasselmann et al., 2001, *Oncol. Rep.* 8: 115-118; Ng et al., 2002, *Clin, Chem.* 48: 1212-1217; Chen et al., 2000, *Clin. Cancer Res.* 6: 3823-3826; Silva et al., 2001, *Clin. Cancer Res.* 7: 2821-2825; Silva et al., 2001, *Oncol. Rep.* 8: 693-696; Gal et al., 2001, *Ann. NY Acad. Sci.* 945: 192-194; Durie et al., 2000, *Acta Oncol.* 39: 789-796; Fleischhacker et al., 2001, *Ann. NY Acad. Sci.* 945: 179-188; Miura et al., 2003, *Oncology* 64: 430-434; and Kopreski et al., 2001, *Ann. NY Acad. Sci,* 945: 172-178, said references incorporated herein in their entirety. Detection of tumor-associated RNA in plasma or serum thus provides a method for detecting, diagnosing, inferring, or monitoring cancer or premalignancy in a human or animal.

Thus, extracellular total RNA is increased in the plasma, serum, or other bodily fluid of humans or animals with cancer and other disease. Thus, there is a need in the art for methods of comparing the amount or concentration of plasma or serum total RNA, including both tumor and non-tumor related RNA, in a subject to that of healthy individuals, to permit diagnosis, detection, inference, or monitoring of diseases such as cancer in a human or animal that are associated with increased extracellular total RNA in said bodily fluids. Further, there is a need for methods comparing the amount or concentration of either total extracellular RNA or non-tumor extracellular RNA species or tumor-related extracellular RNA species from a bodily fluid to that in a healthy individual for diagnosing, detecting, inferring, or monitoring cancer and other neoplastic diseases in a human or animal.

SUMMARY OF THE INVENTION

The invention provides methods for diagnosing, detecting, inferring, evaluating, or monitoring disease, and particularly cancer or other neoplastic disease, in a human or animal, by determining the amount, concentration, or other quantitative or comparative assessment of extracellular total RNA, or of one or more specific RNA species, wherein the RNA species may be either non-tumor related RNA or tumor-related RNA, in a plasma, serum, or bodily fluid specimen from the human or animal. Comparison of the qualitative or quantitative amount or concentration of RNA from said human or animal specimen is made to a comparative specimen RNA assessment, wherein said assessment may comprise a set of previously determined reference range values, to one or a plurality of any of the following reference groups: a healthy human or animal; a human or animal population without cancer; a human or animal with cancer or neoplastic disease; a human or animal population with cancer; a human or animal population with neoplastic disease; a human or animal population with metastatic or advanced cancer; or a previous specimen from the human or animal under evaluation. If the amount or concentration of total extracellular RNA or a specific extracellular RNA species from the bodily fluid of the human or animal is demonstrated to be greater than the amount or concentration present in a healthy human or animal, more specifically a human or animal without cancer, then disease, and particularly cancer or neoplastic disease, is demonstrated or inferred in the evaluated human or animal. Similarly, if the amount or concentration of total extracellular RNA or a specific extracellular RNA species from the bodily fluid of the human or animal is demonstrated to be in the range of a similar amount or concentration found in the comparative specimen of a human or animal or population with cancer, then cancer or neoplastic disease is established in the evaluated human or animal. The methods provided by the invention comprise qualitative or quantitative determination of the amount or concentration of total extracellular RNA or specific extracellular RNA species in a bodily fluid specimen by any of means known to the art, including but not limited to nucleic acid amplification, signal amplification, spectroscopy including mass spectroscopy, and hybridization methods using detectably-labeled probes.

According to a first aspect of the present invention, there is provided methods for detecting, diagnosing, inferring, or monitoring disease, particularly cancer or neoplastic disease in a human or animal, the method comprising the steps of extracting total extracellular RNA from plasma or serum or other bodily fluid specimen of the human or animal, determining quantitatively or qualitatively the amount or concentration of total extracellular RNA from a fraction of said specimen, comparing said amount or concentration of extracellular RNA obtained from the fraction of said specimen to the amount or concentration of extracellular RNA in reference group, wherein said comparison thereby detects, diagnoses, infers, or monitors a cancer or neoplastic disease in a human or animal. In preferred embodiments, the reference group is a human or human population of individuals without cancer, and cancer or neoplastic disease is detected, diagnosed or inferred when the amount or concentration of total extracellular RNA in the fraction of the specimen is greater than the amount or concentration of total extracellular RNA found in the reference group. In alternative preferred embodiments, the reference group is a human or human population of individuals with cancer, and cancer or neoplastic disease is detected, diagnosed or inferred when the amount or concentration of total extracellular RNA in the fraction of the specimen in not significantly less than the amount or concentration of total extracellular RNA found in the reference group.

According to another aspect of the present invention, there is provided methods for detecting, diagnosing, inferring, or monitoring disease, particularly cancer or neoplastic disease in a human or animal, the method comprising the steps of extracting total extracellular RNA from plasma or serum or other bodily fluid specimen of the human or animal, determining quantitatively or qualitatively the amount or concentration of one or a plurality of extracellular RNA species from a fraction of said specimen, comparing said amount or concentration of one or a plurality of extracellular RNA species obtained from the fraction of said specimen to the amount or concentration of one or a plurality of corresponding extracellular RNA species in reference group, wherein said comparison thereby detects, diagnoses, infers, or monitors a cancer or neoplastic disease in a human or animal. In preferred embodiments, the reference group is a human or human population of individuals without cancer, and cancer or neoplastic disease is detected, diagnosed or inferred when the amount or concentration of one or a plurality of extracellular RNA species in the fraction of the specimen is greater than the amount or concentration of one or a plurality of extracellular RNA species found in the reference group. In alternative preferred embodiments, the reference group is a human or human population of individuals with cancer, and cancer or neoplastic disease is detected, diagnosed or inferred when the amount or concentration of one or a plurality of extracellular RNA species in the fraction of the specimen is not significantly less than the amount or concentration of one or a plurality of extracellular RNA species found in the reference group.

According to another aspect of the present invention, there are provided methods for detecting, diagnosing, inferring, or monitoring cancer or neoplastic disease in a human or animal, the method comprising the steps of obtaining a plasma or serum specimen from the human or animal, determining directly on a portion of said specimen the amount or concentration of total extracellular RNA in a portion of the plasma or serum specimen, comparing said amount or concentration to that of a reference group, wherein said comparison thereby detects, diagnoses, infers, or monitors a cancer or neoplastic disease in a human or animal. In preferred embodiments, the reference group is a human or human population of individuals without cancer, and cancer or neoplastic disease is detected, diagnosed or inferred when the amount or concentration of total extracellular RNA in the fraction of the specimen is greater than the amount or concentration of total extracellular RNA found in the reference group. In alternative preferred embodiments, the reference group is a human or human population of individuals with cancer, and cancer or neoplastic disease is detected, diagnosed or inferred when the amount or concentration of total extracellular RNA in the fraction of the specimen is not significantly less than the amount or concentration of total extracellular RNA found in the reference group.

Alternatively, the invention provides methods for detecting, diagnosing, inferring, or monitoring cancer or neoplastic disease in a human or animal, the method comprising the steps of obtaining a plasma or serum specimen from the human or animal, determining directly on a portion of said specimen the amount or concentration of one or a plurality of extracellular RNA species in a portion of the plasma or serum specimen, comparing said amount or concentration to that of a reference group, wherein said comparison thereby detects, diagnoses, infers, or monitors a cancer or neoplastic disease in a human or animal. In preferred embodiments, the reference group is a human or human population of individuals without cancer, and cancer or neoplastic disease is detected, diagnosed or inferred when the amount or concentration of one or a plurality of extracellular RNA species is the fraction of the specimen in greater than the amount or concentration of one or a plurality of extracellular RNA species found in the reference group. In alternative preferred embodiments, the reference group is a human or human population of individuals with cancer, and cancer or neoplastic disease is detected, diagnosed or inferred when the amount or concentration of one or a plurality of extracellular RNA species in the fraction of the specimen is not significantly less than the amount or concentration of one or a plurality of extracellular RNA species found in the reference group.

In a preferred embodiment of the inventive methods, the bodily fluid is blood, plasma, serum, urine, effusions including pleural effusions, ascitic fluid, saliva, cerebrospinal fluid, gastrointestinal secretions, bronchial secretions including sputum, cervical secretions, or breast secretions. In a particularly preferred embodiment, the bodily fluid is plasma or serum.

In preferred embodiments of the inventive methods, the amount of total extracellular RNA, or one or a plurality of extracellular RNA species, is determined quantitatively or qualitatively using a method that is nucleic acid amplification, signal amplification, spectroscopy including mass spectroscopy, or hybridization, preferably to a detectably-labeled probe.

In preferred embodiments of the inventive methods, RNA is extracted from blood, plasma, serum, or other bodily fluid using an extraction method that is a gelatin extraction method; a silica, glass bead, or diatom extraction method; guanidinium thiocyanate acid-phenol based extraction methods; guanidinium thiocyanate acid based extraction methods; phenol-chloroform based extraction methods; by centrifugation through a cesium chloride or similar gradient; or using commercially-available RNA extraction methods, most preferably as provided in a kit comprising instructions from the kit manufacturer.

In preferred embodiments of the invention, RNA extracted from plasma, serum, or other bodily fluid is reverse transcribed to cDNA prior to detection or amplification and detection. In these embodiments, the amount or concentration of RNA is determined by qualitative or quantitative analysis of cDNA or amplified cDNA product.

In preferred embodiments of the invention, extracted RNA or the corresponding cDNA is amplified qualitatively or quantitatively to determine the amount or concentration of a RNA species, using an amplification method that is, for example, polymerase chain reaction, or reverse transcriptase polymerase chain reaction; ligase chain reaction; DNA or RNA signal amplification; amplifiable RNA reporter methods; Q-beta replication; transcription-based amplification; isothermal nucleic acid sequence based amplification; self-sustained sequence replication assays; boomerang DNA amplification; strand displacement activation; cycling probe technology; and any combination or variation thereof.

In preferred embodiments of the inventive methods, detection of amplified RNA or cDNA product is performed using a detection method that is, for example, gel electrophoresis; enzyme-linked immunosorbent assay (ELBA), including embodiments comprising biotinylated or otherwise modified amplification primers; hybridization using a specific, detectably-labeled probe, for example, a fluorescent-, radioisotope-, or chromogenically-labeled probe; Southern blot analysis; Northern blot analysis; electrochemiluminescence; reverse dot blot detection; high-performance liquid chromatography; and variations thereof.

The methods of the invention particularly provide methods for identifying humans at risk for developing a disease, particularly cancer or other neoplastic disease, or who have a malignancy or premalignancy. The methods of the invention thus provide methods for identifying humans having a malignancy such as breast, ovarian, lung, cervical, colorectal, gastric, pancreatic, bladder, endometrial, brain, kidney, or esophageal cancers, leukemias, lymphomas, melanoma, or sarcomas; and premalignancies including but not limited to colorectal adenoma, cervical dysplasia, cervical intraepithelial neoplasia (CIN), bronchial dysplasia, atypical hyperplasia of the breast, ductal carcinoma in-situ, atypical endometrial hyperplasia, and Barrett's esophagus.

The invention thus permits the presence of cancerous (malignant) or pre-cancerous (premalignant) cells within a human or animal to be detected or inferred by determining an amount or concentration of RNA in the plasma, serum, or other bodily fluid of said human or animal that exceeds the amount or concentration normally present in the plasma, serum, or other bodily fluid of a human or animal without cancer or pre-malignancy.

The invention also permits the existence of a disease within a human or animal to be detected or inferred by determining an amount or concentration of RNA in the plasma, serum, or other bodily fluid of said human or animal that exceeds the amount or concentration normally present in the plasma, serum, or other bodily fluid of a healthy human or animal.

An advantageous application of this invention is to identify humans or animals with disease.

It is a particularly advantageous application of this invention to identify humans or animals having cancer.

Another advantageous application of this invention is to identify humans or animals having risk for developing cancer.

Another advantageous application of this invention is to identify humans or animals having a premalignant disease.

Another advantageous application of this invention is for monitoring cancer, including response to cancer therapies.

Another advantageous application of this invention is selecting humans or animals for cancer therapies, including surgery, biotherapy, hormonal therapy, anti-sense therapy, monoclonal antibody therapy, chemotherapy, vaccines, anti-angiogenic therapy, cryotherapy, and radiation therapy.

Another advantageous application of this invention is to provide a marker as a guide to whether adequate therapeutic effect has been achieved, or whether additional or more advanced therapy is required, and to assess prognosis in a patient.

Another advantageous application of this invention is to provide an indicator of a relapsed cancer following therapy, or impending relapse, or treatment failure.

Another advantageous application of this invention is to identify humans or animals who might benefit from additional diagnostic procedures, wherein said procedures include but are not limited to surgery, biopsy, needle aspiration, radiologic imaging including X-ray, MRI, and CT scanning, radionucleotide imaging, colonoscopy, sigmoidoscopy, bronchoscopy, endoscopy, PET scanning, stool analysis, sputum analysis, cystoscopy, pelvic examination, and physical examination.

The invention also provides diagnostic kits enabling quantitative or qualitative assessment of total RNA or specific RNA species in plasma or serum, wherein a reference range for normal values or cancer values is provided to enable identification or selection of a human or animal with or at risk for cancer.

Specific preferred embodiments of the present invention will become evident from the following more detailed description of certain preferred embodiments and the claims.

DETAILED DESCRIPTION OF THE INVENTION

This invention relates to methods for detecting, diagnosing, inferring, or monitoring cancer or neoplastic disease in a human or animal by assessing the amount or concentration of RNA, particularly extracellular RNA, in plasma, serum, or other bodily fluid from said human or animal, and comparing the amount or concentration of extracellular RNA obtained from the human or animal with the amount or concentration of RNA found for a reference individual, group or population of known disease status. In particular, the invention provides methods for detecting, inferring or monitoring the presence of cancerous or precancerous cells in a human or animal, whether from a non-hematologic neoplasm (i.e., a solid-tumor) or from a hematologic malignancy (such as leukemia, lymphoma, myeloma, etc.). The methods of the invention determine an amount, concentration or other quantitative or comparative assessment of RNA from a bodily fluid specimen obtained from a human or animal, wherein the RNA can be either total extracellular RNA, or one or a plurality of specific RNA species or multiple specific RNA species. RNA species may be either tumor-related RNA or non-tumor related RNA. Total extracellular RNA will be recognized as comprising both tumor-related and non-tumor-related RNA when obtained from a patient with cancer or other neoplastic disease. In preferred embodiments, the bodily fluid is blood, plasma, serum, urine, effusions including pleural effusions, ascitic fluid, saliva, cerebrospinal fluid, gastrointestinal secretions, bronchial secretions including sputum, cervical secretions, or breast secretions. Plasma and serum are particularly preferred bodily fluids, but any bodily fluid comprising extracellular RNA, and particularly disease-associated extracellular RNA is useful in the practice of the methods of this invention.

As used herein, the terms "disease-associated," "disease-related," "tumor-related" and "non-tumor-related" are intended to encompass particular RNA species, as well as total extracellular RNA. It will be understood that certain RNA species, such as oncogenic RAS, p53, and other RNA species, are recognized in the art as being associated with the existence of cells comprising a disease state, particularly neoplastic disease, malignancy or premalignancy. RNA species are "disease-associated," "disease-related," "tumor-related" when their presence as a component of total extracellular RNA is indicative of the existence of a disease, particularly a neoplastic disease. "Non-tumor-related" RNA species, on the other hand, comprise RNA species component(s) present in healthy individuals; such species may also be present in individuals bearing disease-associated, disease-related, or tumor-related extracellular RNA species as well. It will be recognized that in certain embodiments of the methods of this invention, detecting a lack of expression of an RNA species comprising non-tumor-related RNA may indicate the existence of disease in said human or animal.

As used herein, the term "quantitative" when applied to an amplification method or to detection of total extracellular RNA or one or a plurality of RNA species thereof is intended to indicate that the method or determination performed provides an accurate, reliable and reproducible measure of the amount or concentration of total extracellular RNA or one or a plurality of RNA species thereof, based on a calculated or experimentally-determined measurement of the amount or concentration of total extracellular RNA or one or a plurality of RNA species thereof. In preferred embodiments, the method includes amplification of a standard or control RNA species that is used to determine the amount or concentration of total extracellular RNA or one or a plurality of RNA species thereof.

As used herein, the term "qualitative" when applied to an amplification method or to detection of total extracellular RNA or one or a plurality of RNA species thereof is intended to indicate that the method or determination performed provides a relative measure of the amount or concentration of total extracellular RNA or one or a plurality of RNA species thereof, based on a comparison of the amount or concentration of total extracellular RNA or one or a plurality of RNA species thereof.

Qualitative or quantitative comparison of the amount or concentration of RNA from said human or animal bodily fluid specimen is made in comparison to an RNA specimen or standard from a reference individual, group, or population. Said assessment is made on the basis of a previously-determined reference set of values for said individual, group or population, or alternatively upon a newly determined reference set of values for the individual, group, or population. Comparison to the reference individual, group, or population thereby enables determination of the likelihood that the subject human or animal has a disease, particularly cancer or neoplastic disease such as premalignancy, wherein if the amount or concentration (or similar comparative RNA indicator) of total extracellular RNA or of one or a plurality of specific RNA species thereof from the bodily fluid of the subject human or animal is demonstrated to be greater than the amount or concentration (or similar comparative indicator) present in individuals, groups, or populations without disease, particularly cancer or neoplastic disease, then a disease, particularly cancer or an increased risk of cancer (for example, due to the existence of a premalignancy) will be inferred in the human or animal subject. Similarly, if the amount or concentration of total extracellular RNA, or of one or a plurality of specific RNA species thereof in the bodily fluid of the subject is within the range of a group or population with a disease, particularly cancer or neoplastic disease such as a premalignancy, then a disease, particularly cancer or an increased risk of cancer (for example, due to the existence of a premalignancy) will be inferred in the human or animal subject. If the amount or concentration of total extracellular RNA, or of one or a plurality of specific RNA species thereof in the bodily fluid of the subject is less than the range for patients with cancer, or within the range of the healthy population, then the risk of disease, particularly cancer or an increased risk of cancer (for example, due to the existence of a premalignancy) will be less. It will be recognized that the limits of the reference range values may be set in a manner that determines a sensitivity or specificity or positive predictive value or negative predictive value for the assay, or otherwise provides the probability of the assay correctly identifying a subject with cancer or neoplasm. Thus, in this manner the reference range for a group or population can be defined that increases the sensitivity or specificity of the assay.

It is to be recognized that a variety of individuals, groups, or populations will provide suitable reference values that enable discrimination of abnormal (disease-, and more particularly cancer-, related) and normal amounts or concentrations of total extracellular RNA, or of one or a plurality of specific RNA species thereof in the bodily fluid of the subject. Appropriate reference individuals, groups, or populations include but is not limited to: a healthy human or animal, more specifically a human or animal population without neoplastic disease (cancer or premalignancy) or a human or animal population without cancer; a human or animal population with a disease, more specifically a human or animal population with neoplastic disease (cancer or premalignancy) or a human or animal population with cancer; a previously-isolated bodily fluid specimen from the human or animal under evaluation corresponding to a known disease or health state. In addition, it will be recognized that certain defined groups or populations will provide useful reference values to assess probability of disease, particularly cancer or premalignancy, in a subject, including but not limited to: groups and populations defined by gender and the presence or absence of disease, particularly cancer or premalignancy; groups and populations defined by race or ethnicity and presence or absence of disease, particularly cancer or premalignancy; groups and populations defined by non-neoplastic diseases; groups and populations defined by specific tumor types; groups and populations defined by stage or extent of cancer of a particular type; groups and populations defined by certain environmental or occupational risks for cancer, such as smokers or workers occupationally exposed to carcinogens; and groups and populations defined by genetic or family risk for cancer. It is to be understood that the comparative assessment of the subject's total extracellular RNA in a bodily fluid such as blood plasma or serum to reference groups and populations may be made by either non-statistical or statistical analysis, as is known to the art.

In particularly preferred embodiments of the invention, the bodily fluid is blood plasma or serum. Either fresh never frozen) blood plasma or serum, or frozen (stored) and subsequently thawed plasma or serum may be used for purposes of these embodiments. In a preferred embodiment the blood is processed soon after drawing, preferably within 24 hours and most preferably within 6 hours, to minimize any degradation of nucleic acids. While early processing is not a requirement of the methods of the invention, it will be recognized that variations of early processing can be employed as set forth below, without limitation implied. In one aspect, the blood may be initially processed to stabilize the RNA or to stabilize phospholipids encapsulating the extracellular RNA, or to inhibit nucleases present in blood, Stabilizing agents or inhibitors may be provided within kits according to the invention or within venipuncture tubes or devices. Such initial processing is useful if specimen transport or work schedules will result in processing delays. In another aspect, initial processing may be performed by hybridizing the RNA or binding associated apoptotic bodies or other RNA encapsulated particles to solid substrates shortly after venipuncture, preferably using reagents provided in a kit of this invention or as part of specialized blood collection systems. It is preferred that the processing of the specimen from the human or animal subject and from the reference group or population be handled in a similar or like manner to the extent practical, or alternatively the effect due to variations in specimen processing defined and comparisons appropriately adjusted.

In a preferred embodiment, blood is first collected by venipuncture and kept on ice until serum or plasma is separated from whole blood, for example using centrifugation methods gentle enough not to lyse blood cells. While a considerable range of centrifugation speeds may be employed, centrifugation at high speeds (such as beyond 100,000×g) for prolonged periods should be avoided to prevent clearance of RNA-containing apoptotic bodies or other encapsulated extracellular RNA particles from the supernatant Non-limiting examples of suitable conditions is centrifuging a blood specimen at a range of 300 to 5,000×g for five to thirty minutes, or fractionating by other standard methods to produce plasma or serum will suffice, Sera or plasma obtained in this manner can be assayed directly, or stored frozen, for example at −20 to −80 degrees centigrade until further analysis according to the methods of this invention.

In a preferred embodiment of the invention, extracellular RNA in plasma or serum or other bodily fluid of the human or animal is assayed by extracting total extracellular RNA from plasma or serum or other bodily fluid of the human or animal, determining quantitatively or qualitatively the amount or concentration of total extracellular RNA, or one or a plurality of specific RNA species thereof comprising a portion of the total extracellular RNA, and comparing said amount or concentration obtained from the human or animal to the total extracellular RNA, or one or a plurality of specific RNA species thereof from a reference group, wherein said comparison detects, diagnoses, infers, or monitors a disease, particularly cancer or neoplastic disease in the human or animal. Bodily fluids are preferably separated into essentially cellular and non-cellular components, using centrifugation or other fractionation techniques, and total extracellular RNA thereafter extracted from the non-cellular components.

In the practice of the methods of this invention, total extracellular RNA can be extracted from bodily fluid using methods well-known to the art, including but not limited to gelatin extraction method; silica, glass bead, or diatom extraction method; guanidinium thiocyanate acid-phenol based extraction methods; guanidinium thiocyanate acid based extraction methods; centrifugation through a cesium chloride or similar gradient; phenol-chloroform based extraction methods; hybridization and immunobead separation; or commercially available RNA extraction methods. Methods of RNA extraction are further provided in U.S. Pat. No. 6,329,179 B1, incorporated herein in its entirety by reference. If plasma or serum had been previously frozen, upon assay it should be thawed rapidly, for example in a warm water bath at about 37 degrees centigrade, and thereafter RNA rapidly extracted to minimize degradation thereof.

However, it should be understood that extraction of total extracellular RNA is not a requirement for the practice of the methods of this invention. In some embodiments, methods such as spectroscopic methods including mass spectroscopy, and cytometry can be used for direct analysis of total extracellular RNA or RNA encapsulated particles within the bodily fluid.

The amount or concentration of total extracellular RNA from the bodily fluid is determined quantitatively or qualitatively using nucleic acid (RNA or cDNA) amplification, signal amplification, spectroscopy including mass spectroscopy, or hybridization to a detectably-labeled probe. In a preferred embodiment, a portion of the extracted total extracellular RNA is amplified or signal amplified qualitatively or quantitatively. Total extracellular RNA extracted from blood plasma or serum or other bodily fluid may first be reverse transcribed to cDNA, whereupon the cDNA is amplified or signal amplified qualitatively or quantitatively. In preferred embodiments, amplification is performed using primers or probes that are specific for particular RNA or cDNA species, wherein the RNA or its cDNA may be a non-tumor related RNA or a tumor-related RNA. Non-tumor RNA include but are not limited to housekeeper gene RNA, and non-limiting examples of non-tumor RNA include RNA encoding all or a portion of c-abl, porpho-bilinogen deaminase (PBDG), glyceraldehyde 3-phosphate dehydrogenase (GAPDH), retinoic acid receptor (RAR), and β-actin. Examples of tumor-related or tumor-associated RNA not intending to be limiting include tyrosinase RNA, keratin RNA species, prostate specific antigen RNA, alpha-fetoprotein RNA, BCR/abl RNA, carcinoembryonic antigen RNA, p97 RNA, p16 RNA, MUC 18 RNA, PML/RAR RNA, CD44 RNA, EWS/FLI-1 RNA, EWS/ERG RNA, AML1/ETO RNA, MAGE RNA species, beta human chorionic gonadotropin RNA, telomerase-associated RNA including TEP1 RNA, human telomerase RNA template (hTR) RNA and telomerase reverse transcriptase protein (hTERT) RNA, bcl-2 RNA, bax RNA, survivin RNA, COX-2 RNA, P5.3 RNA, c-myc RNA, her-2/neu RNA, Von Hippel-Lindau gene RNA, retinoblastoma gene RNA, mutated in colon cancer (MCC) gene RNA, adenomatous polyposis coli (APC) gene RNA, deleted in colon cancer (DCC) gene RNA, epidermal growth factor receptor (EGFR) RNA, epidermal growth factor (EGF) RNA, hn RNP-A1 RNA, hn RNP-A2/B1 RNA, hn RNP-K RNA, 5T4 RNA, DNA methyltransferase RNA, matrix metalloproteinase species RNA, mammaglobin RNA, DD3(PCA3) RNA, glutathione S-transferase RNA, MDR-1 RNA, and JC virus RNA. It will be recognized that the above examples are not intended to be limiting, and any non-tumor or tumor-related RNA species or corresponding cDNA may be detected according to the methods of this invention. Further, it will be recognized that various RNA species are well known to the art, and that the scope of the invention is meant to encompass these RNA species without limitation.

Various amplification methods or signal amplification methods are known in the art and can be used in accordance with the methods of this invention. In preferred embodiments of the methods of the invention, quantitative or qualitative amplification is performed using an amplification or signal amplification method such as polymerase chain reaction; reverse transcriptase polymerase chain reaction; ligase chain reaction; DNA or RNA signal amplification; amplifiable RNA reporters; Q-beta replication; transcription-based amplification; isothermal nucleic acid sequence based amplification; self-sustained sequence replication assays; boomerang DNA amplification; strand displacement activation; cycling probe technology; or any combination or variation thereof. In one aspect of this embodiment, quantitative amplification is performed using the Taqman technology (Perkin Elmer Biosystems), with primers for the target RNA using a dye-labeled internal primer.

In preferred embodiments, following amplification the RNA or cDNA amplified or signal amplified product is detected in a quantitative or qualitative manner by methods known to the art. In preferred embodiments of the inventive methods, detection of amplified RNA or cDNA product is performed using a detection method selected from a group consisting of gel electrophoresis; ELISA detection including modifications, including biotinylated or otherwise modified primers; hybridization using a specific, fluorescent-, radio-isotope-, or chromogenically-labeled probe; Southern blot analysis; Northern blot analysis; electrochemiluminescence; reverse dot blot detection; and liquid chromatography, including high-performance liquid chromatography.

Upon amplification and detection of total extracellular RNA or one or a plurality of specific RNA species, most preferably wherein one or a plurality of species of total extracellular RNA is a disease- or tumor-related gene, an amount or concentration or other value allowing comparative assessment is determines, using for example, gel intensity, signal intensity, or color intensity, color, mass, or electrical propensity. Assessment is made to a reference individual, group, or population based upon analysis of said RNA under similar condition and methods, or by extrapolation to similar conditions and methods. If the RNA in the subject specimen is of greater amount, concentration, or other assessment value than that expected for a healthy reference group or population, or within the range for a disease group or population, most preferably a cancer group or population, then disease, most particularly cancer or neoplastic disease, will be thereby diagnosed, detected, inferred, or monitored in the subject human or animal.

In another embodiment of the invention, determination of an amount, concentration, or other comparative assessment is made using total extracellular RNA without amplification prior to detection. For example but not limitation, total extracellular RNA extracted from a bodily fluid may be hybridized and detected without amplification. In this aspect, it is particularly preferred but not required that the extracted RNA be concentrated upon extraction or upon separation from the bodily fluid, using for example immunobead capture or hybridization onto a solid substrate, to improve assay sensitivity. In another aspect of this embodiment, extracellular RNA is evaluated by spectroscopy, for example by mass spectroscopy or magnetic resonance spectroscopy, or by flow cytometry. In one aspect, fluorometric methods may be employed, for example as employed by Kamm and Smith (1972, *Clin. Chem.*, 18: 519-522), said reference incorporated herein in its entirety.

The methods of the invention identify humans or animals bearing or at risk for developing malignancies including but not limited to tumors of breast, ovarian, lung, cervical, colorectal, gastric, pancreatic, bladder, endometrial, head and neck, brain, kidney, and esophageal tissues, as well as leukemias, lymphomas, melanoma, and sarcomas. The methods of the invention may further be utilized to identify humans or animals with premalignancy, including but not limited to colorectal adenoma, cervical dysplasia, cervical intraepithelial neoplasia (CIN), bronchial dysplasia, bronchial metaplasia, atypical hyperplasia of the breast, ductal carcinoma in-situ of the breast, atypical endometrial hyperplasia, prostatic intraepithelial neoplasia, and Barrett's esophagus. The methods of the invention may be applied to a subject of any age, race, ethnicity or gender, although it is preferred that the reference group or population include individuals of similar age (child, adult, elderly) and sex (male, female).

The invention permits detection, diagnosis, and monitoring of disease, particularly cancer and premalignancy, and identification of individuals at risk for developing disease, particularly cancer or neoplastic disease such as premalignancy, providing considerable clinical utility. The invention provides methods to identify, stratify, or select a human or animal that might benefit from a therapy, or from a further diagnostic test. The invention permits disease such as cancer to be monitored, including response to cancer therapies, by providing a marker to guide whether therapeutic effect has been achieved, or if more therapy is required, and to assess prognosis.

An advantageous application of the methods of this invention is to allow selection of humans or animals for cancer therapies including surgery, biotherapy, hormonal therapy, anti-sense therapy, monoclonal antibody therapy, chemotherapy, vaccines, anti-angiogenic therapy, cryotherapy, and radiation therapy.

Another advantageous application of the methods of this invention is to provide an indicator of a relapsed cancer following therapy, or impending relapse, or treatment failure.

Another advantageous application of the methods of this invention is to identify humans or animals who might benefit from additional diagnostic procedures, wherein said procedures include but are not limited to surgery, biopsy, needle aspiration, radiologic imaging including X-ray, MRI, and CT scanning, radionucleotide imaging, colonoscopy, sigmoidoscopy, bronchoscopy, endoscopy, PET scanning, stool analysis, sputum analysis, cystoscopy, pelvic examination including PAP, and physical examination.

The invention further provides diagnostic and research kits that enable quantitative, qualitative or other comparative assessment of total RNA or of specific RNA species in plasma, serum, or other bodily fluids. In one aspect, a kit according to this aspect of the invention can provide a reference range for normal values or values that are disease-related under conditions that enable identification or selection of a human or animal with a disease, most particularly cancer or neoplastic disease. In another aspect kits of this invention provide reagents for extracting total extracellular RNA from the bodily fluid, or reagents and/or probes and primers for the amplification of said RNA, or reagents and materials for the detection of RNA product, or reagents for hybridization of RNA, or standards and controls for the analysis of the test, or reagents or devices or tubes for collecting, handling, or storage of the bodily fluid, or any combination or variation thereof, wherein further the reagents may be standardized to be comparable with reagents used to define RNA values for the reference population.

The methods of the invention and preferred uses for the methods of the invention are more fully illustrated in the following Examples. These Examples illustrates certain aspects of the above-described method and advantageous results. These Examples are shown by way of illustration and not by way of limitation.

Example 1

Defining Reference Values in Human Populations

The presence or absence of tyrosinase RNA in serum was evaluated in qualitative fashion for two human populations, one comprising 20 healthy individuals, and the second comprising 6 patients with malignant melanoma. Total RNA was extracted from serum using a commercial kit (Perfect RNA: Total RNA Isolation Kit, 5 Prime-3 Prime Inc., Boulder, Colo.) according to manufacturer's instructions. The extracted RNA from 50 microliters of serum was then reverse transcribed and tyrosinase cDNA amplified by nested polymerase chain reaction using tyrosinase-specific primers, Amplified product was electrophoresed through a 4% agarose gel in 1×TBE buffer at 100 volts for 2 hours and stained with ethidium bromide and detected. The amount or concentration of tyrosinase RNA in serum was below limits of detection in all 20 healthy individuals. Conversely, 4 of 6 patients with melanoma had detectable tyrosinase RNA in their serum as determined by detection of a tyrosinase-specific amplified fragment of the predicted size. These results thus define the reference value for extracellular tyrosinase RNA in serum from healthy individuals as being either very low in amount and concentration, or as being qualitatively non-detectable. Individuals screened for cancer, particularly melanoma, which demonstrate high or detectable amounts or concentrations of tyrosinase RNA in their serum are thus identified as either having melanoma, or having a high risk for melanoma.

Example 2

Clinical Application

A 52 year-old woman with no symptomatic evidence of disease presents for routine cancer screening. Her physician draws a plasma specimen for assay. Total extracellular RNA is extracted from the patient's plasma, and the extracted extracellular RNA amplified quantitatively using Taqman PCR technology for a housekeeping gene RNA or similar standard RNA such as c-abl RNA. In this case the woman's quantitative levels of c-abl RNA exceeds the normal reference range of c-abl RNA in plasma from healthy patients without cancer. The presence of cancer, or a high risk of developing cancer, is therefore identified for the woman, and the physician is indicated to perform additional diagnostic testing to further define the extent and nature of the woman's cancer.

It should be understood that the foregoing disclosure emphasizes certain specific embodiments of the invention and that all modifications or alternatives equivalent thereto are within the spirit and scope of the invention as set forth in the appended claims.

What is claimed is:

1. A method for evaluating whether a human is at risk for a neoplastic disease or neoplastic condition, the method comprising the steps of:
  a) obtaining blood plasma or serum from a human;
  b) extracting RNA from the blood plasma or serum from the human, wherein a portion of the RNA comprises two or more different human tumor-associated RNA species;
  c) amplifying or signal amplifying said two or more different tumor-associated RNA species, or cDNAs derived therefrom from said portion of the RNA of the human using primers or labeled probes specific for said two or more different tumor-associated RNA species or cDNAs derived therefrom and producing two or more different amplified or signal labeled amplified products;
  d) independently amplifying or signal amplifying said two or more different tumor-associated RNA species, or cDNAs derived therefrom from a portion of RNA extracted from blood plasma or serum of a human without said neoplastic disease or neoplastic condition using said primers or labeled probes specific for said two or more different tumor-associated RNA species or cDNAs derived therefrom; and
  e) comparing the amounts or concentrations of said two or more different tumor-associated RNA species in the blood plasma or serum from the human with the amounts of said two or more different tumor-associated RNA species in the blood plasma or serum from the human without said neoplastic disease or neoplastic condition based on the amounts of the two or more different amplified products produced from step c) and the amounts of two or more different amplified products produced from step d), wherein the human is at risk for said neoplastic disease or neoplastic condition when the amounts or concentrations of said two or more different tumor-associated RNA species in the blood plasma or serum from the human are significantly greater than the amounts or concentrations of said two or more different tumor-associated RNA species in the blood plasma or serum from the human without said neoplastic disease or neoplastic condition.

2. The method according to claim 1, wherein the amplified products produced from step c) and amplified products produced from step d) are detected using gel electrophoresis, enzyme-linked immunosorbent assay (ELISA), fluorescent-labeled probes, radioisotope-labeled probes, chromogenically-labeled probes, Southern blot analysis, Northern blot analysis, electrochemiluminescence, reverse dot blot, or liquid chromatography.

* * * * *